United States Patent [19]

Bowers et al.

[11] Patent Number: 5,486,505

[45] Date of Patent: Jan. 23, 1996

[54] POLYPEPTIDE COMPOUNDS HAVING GROWTH HORMONE RELEASING ACTIVITY

[75] Inventors: Cyril Y. Bowers, New Orleans, La.; Wayne L. Cody, Saline, Mich.; John C. Hubbs; Charles H. Foster, both of Kingsport, Tenn.; Frank A. Momany, Wellesley, Mass.

[73] Assignee: Polygen Holding Corporation, Wilmington, Del.

[21] Appl. No.: 962,069

[22] Filed: Oct. 16, 1992

Related U.S. Application Data

[63] Continuation of Ser. No. 557,226, Jul. 24, 1990, abandoned.

[51] Int. Cl.⁶ .................. A61K 38/00; C07K 7/06
[52] U.S. Cl. ........................... 514/16; 530/328
[58] Field of Search .................. 514/16; 530/328

[56] References Cited

U.S. PATENT DOCUMENTS 4,228,157 10/1980 Momany ............................ 514/17
4,410,512 10/1983 Bowers ............................. 514/17
4,411,890 10/1983 Momany ............................ 514/17
4,839,344 6/1989 Bowers et al. ..................... 514/16
4,880,778 11/1989 Bowers et al. ..................... 514/12

FOREIGN PATENT DOCUMENTS

| 0018072 | 10/1980 | European Pat. Off. . |
| WO87/06835 | 11/1987 | WIPO . |
| WO89/09780 | 12/1988 | WIPO . |
| WO89/07111 | 8/1989 | WIPO . |
| WO89/07110 | 8/1989 | WIPO . |
| WO89/10933 | 11/1989 | WIPO . |

*Primary Examiner*—Jill Warden
*Assistant Examiner*—S. G. Marshall
*Attorney, Agent, or Firm*—Ronald I. Eisenstein

[57] ABSTRACT

Novel polypeptides which promote the release of growth hormone when administered to animals are described. These polypeptides have the formula:

$$A_1-D^\beta Nal-A_3-Trp-A_5-A_6-Z$$

wherein $A_1$, $A_3$, $A_5$, $A_6$ and $Z''$ are as defined in the specification.

24 Claims, No Drawings

POLYPEPTIDE COMPOUNDS HAVING GROWTH HORMONE RELEASING ACTIVITY

This is a continuation of application Ser. No. 07/557,226 filed on Jul. 24, 1990, now abandoned.

This invention relates to novel polypeptide compounds which promote the release of growth hormone when administered to animals. In another aspect, this invention relates to methods for promoting the release and elevation of growth hormone levels in animals by administration of specified growth hormone releasing polypeptide compounds thereto.

BACKGROUND OF THE INVENTION

The elevation of growth hormone (GH) levels in mammals upon administration of GH-releasing compounds can lead to enhanced body weight and to enhanced milk production if sufficiently elevated GH levels occur upon administration. Further, it is known that the elevation of growth hormone levels in mammals can be accomplished by application of known growth hormone releasing agents, such as the naturally occurring growth hormones releasing hormones.

The elevation of growth hormone levels in mammals can also be accomplished by application of growth hormone releasing peptides, some of which have been previously described, for example, in U.S. Pat. No. 4,223,019, U.S. Pat. No. 4,223,020, U.S. Pat. No. 4,223,021, U.S. Pat. No. 4,224,316, U.S. Pat. No. 4,226,857, U.S. Pat. No. 4,228,155, U.S. Pat. No. 4,228,156, U.S. Pat. No. 4,228,157, U.S. Pat. No. 4,228,158, U.S. Pat. No. 4,410,512, U.S. Pat. No. 4,410,513, U.S. Pat. No. 4,411,890 and U.S. Pat. No. 4,839,344.

Antibodies to the endogenous growth hormone release inhibitor, somatostatin (SRIF) have also been used to cause elevated GH levels. In this latter example, growth hormone levels are elevated by removing the endogenous GH-release inhibitor (SRIF) before it reaches the pituitary, where it inhibits the release of GH.

Each of these methods for promoting the elevation of growth hormone levels involve materials which are expensive to synthesize and/or isolate in sufficient purity for administration to a target animal. Short chain, relatively simple polypeptides which have the ability to promote the release of growth hormone would be desirable because they should be readily and inexpensively prepared, easily modified chemically and/or physically, as well as easily purified and formulated; and they should have excellent transport properties.

It would be desirable to have short chain polypeptides which promote the release and elevation of growth hormone levels in the blood of animals. It would also be useful to be able to use such polypeptides to promote the release and elevation of growth hormone levels in the blood of animals.

SUMMARY OF THE INVENTION

We have now discovered several novel polypeptide compounds which promote the release of growth hormone in animals. These polypeptides have the formula $A_1$—$D^\beta Nal$—$A_3$—Trp—$A_5$—$A_6$—Z wherein $A_1$ is His, 3(NMe)His, $A_0$—His, $A_0$—3(NMe)His, Ala, Tyr or His—Ala, wherein $A_0$ is any naturally occurring L-amino acid, Met(O), DOPA, Abu, or peptides of the formula, L—$A_0$, wherein L is H, DOPA, Lys, Phe, Tyr, Cys, Tyr—DAla—Phe—Gly, Tyr—DAla—Gly—Phe, Tyr—Ala—Gly—Thr or Tyr—DAla—Phe—Sar, preferably $A_0$ is any naturally occurring amino acid, more preferably, $A_0$ is Ala, Lys, or Glu; $A_3$ is Ala, Gly or Ser; $A_5$ is DPhe, D/L$^\beta$(Me)Phe or (NMe)DPhe; $A_6$ is B-G or G, wherein B is any naturally-occurring amino acid, dipeptides of any naturally-occurring amino acids or $H_2N$—$(CH_2)_n$—$CO_2H$ (wherein n= 2–12) and G is Arg, iLys, or Orn; Z is the C terminal end group —$CONR^1R^2$, —$COOR^1$ or —$CH_2OR^1$ (wherein $R^1$ is H, an alkyl group having from 1 to about 6 carbon atoms, a cycloalkyl group having from 3 to about 8 carbon atoms, an alkenyl group having from 2 to about 8 carbon atoms or an aryl group having from 6 to about 12 carbon atoms, and $R^2$ is defined as $R^1$ and may be the same or different), —Gly—Z', —Met—Z', —Lys—Z', —Cys—Z', —Gly—Tyr—Z', or —Ala—Tyr—Z', wherein Z' is —$CONR^1R^2$, —$COOR^1$ or —$CH_2OR^1$ (wherein $R^1$ and $R^2$ are as defined above), and the organic or inorganic pharmaceutically acceptable salts thereof. Preferably, the peptide has the formula His—$D^\beta Nal$—Ala—Trp—DPhe—Lys—$NH_2$, $A_0$—His—$D^\beta Nal$—Ala—Trp—DPhe—Lys—$NH_2$ (for example Ala—His—$D^\beta Nal$—Ala—Trp—DPhe—Lys—$NH_2$) or Ala—$D^\beta Nal$—Ala—Trp—DPhe—Lys—$NH_2$.

Such peptides can be used to promote the release and elevation of blood growth hormone levels in animals, preferably, humans, by administering an effective amount of the peptide.

DETAILED DESCRIPTION OF THE INVENTION

The present invention is based on the discovery of several short chain polypeptides which promote the release and elevation of growth hormone levels in the blood of animals. The polypeptides contemplated to be within The scope of the present invention are defined by the following generic structure:

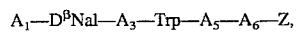

wherein $A_1$, $A_3$, $A_5$, $A_6$ and Z are as defined below. $A_1$ is His, 3(NMe)His (i.e. wherein the imidazole ring is methylated at the 3-position). His—Ale, $A_0$—His, Ala, Tyr or $A_0$—3(NMe)His, where $A_0$ is any naturally occurring L-amino acid, Met(O). DOPA, Abu or peptides of the formula, L—$A_0$, wherein L is H, DOPA, Lys, Phe, Tyr, Cys, Tyr—DAla—Phe—Gly, Tyr—DAla—Gly—Phe, Tyr—Ala—Gly—Thr or Try—DAla—Phe—Sar. Preferably, $A_1$ is His, Ale, His—Ala, $A_0$—His, or Ala. More preferably, $A_1$ is His or $A_0$—His. $A_0$ is preferably any naturally occurring L-amino acid, more preferably, $A_0$ is Ala, Lys or Glu. Still more preferably, $A_0$ is Ala.

$A_3$ is Ala, Gly or Ser. $A_3$ is preferably Ala.

$A_5$ Is DPhe D/L$^{62}$ (Me)Phe or (NMe)DPhe. Preferably, $A_5$ is DPhe.

$A_6$ Is B-G or G, wherein B is any naturally occurring L-amino acid, dipeptides of any naturally occurring L-amino acids (such as Ala—Lys, Ala—Ala, Ala—Leu) or $H_2N$—$(CH_2)_n CO_2H$, wherein n=2–12, and G is Arg, iLys, Lys or Ore. More preferably B is any naturally occurring L-amino acid or $H_2N$—$(CH_2)_n CO_2H$, wherein n=4–8. Still more preferably, $A_6$ is G, Ala—Lys, or Ala—Ala—Lys. Even more preferably, $A_6$ is G. Most preferably, $A_6$ is Lys.

Z represents the C terminal end group of the polypeptide or the C terminal amino acid(s) plus end group, wherein Z is —$CONR^1R^2$, —$COOR^1$ or —$CH_2OR^1$, wherein $R^1$ is H, an alkyl group having from 1 to about 6 carbon atoms, a cycloalkyl group having from 3 to about 8 carbon atoms, an alkenyl group having from 2 to about 8 carbon atoms, or an aryl group having from 6 to about 12 carbon atoms. $R^2$ is defined as $R^1$ and may be the same or different. Preferably, $R^1$ is H or an alkyl group having from 1 to about 6 carbon atoms. Z can also be —Gly—Z', —Met—Z', —Lys—Z', —Cys—Z', —Gly—Tyr—Z', or —Ala—Tyr—Z', wherein Z' is —CONR$^1$R$^2$, —COOR$^1$ or —CH$_2$OR$^1$, wherein $R^1$ and $R^2$ are as defined above. Preferably, Z is —CONR$^1$R$^2$, —COOR$^1$ or —CH$_2$OR$^1$.

And the pharmaceutically acceptable organic or inorganic addition salts of any of said polypeptides.

The amino acid residue abbreviations used are in accordance with the standard peptide nomenclature:

| | | |
|---|---|---|
| Gly | = | Glycine |
| Tyr | = | L-Tyrosine |
| Ile | = | L-Isoleucine |
| Glu | = | L-Glutamic Acid |
| Thr | = | L-Threonine |
| Phe | = | L-Phenylalanine |
| Ala | = | L-Alanine |
| Lys | = | L-Lysine |
| Asp | = | L-Aspartic Acid |
| Cys | = | L-Cysteine |
| Arg | = | L-Arginine |
| Gln | = | L-Glutamine |
| Pro | = | L-Proline |
| Leu | = | L-Leucine |
| Met | = | L-Methionine |
| Ser | = | L-Serine |
| Asn | = | L-Asparagine |
| His | = | L-Histidine |
| Trp | = | L-Tryptophan |
| Val | = | L-Valine |
| DOPA | = | 3,4-Dihydroxyphenylalanine |
| Met(O) | = | Methionine Sulfoxide |
| Abu | = | α-Aminobutyric Acid |
| iLys | = | N$^\epsilon$-Isopropyl-L-Lysine |
| 4-Abu | = | 4-Aminobutyric Acid |
| Orn | = | L-Ornithine |
| D$^\alpha$Nal | = | α-Naphthyl-D-Alanine |
| D$^\beta$Nal | = | β-Naphthyl-D-Alanine |
| Sar | = | Sarcosine |

All three letter amino acid abbreviations preceded by a "D" indicated the D-configuration of the amino acid residue, and abbreviations preceded by a "D/L" indicate a mixture of the D- and L-configurations of the designated amino acid. For purposes of this disclosure, glycine is considered to be included in the term "naturally occurring L-amino acids".

The basic, neutral or acidic amino acid residues that can be used for amino acids $A_1$, $A_3$, $A_5$ and $A_6$ provide one with a great deal of control over the physiochemical properties of the desired peptide. Such flexibility provides important advantages for the formulation and delivery of the desired peptide to any given species. Additional flexibility is gained by the selection of R and Z moieties, as well, thereby providing added control over the physiochemical properties of the desired compound.

Preferred growth hormone releasing compounds employed in the practice of the present invention are:

$A_1$—D$^\beta$Nal—Ala—Trp—DPhe—$A_6$—Z, such as $A_0$—His—D$^\beta$Nal—Ala—Trp—DPhe—$A_6$—Z, His—Ala—D$^\beta$Nal—Ala—Trp—DPhe—$A_6$—Z, Ala—D$^\beta$Nal—Ala—Trp—DPhe—$A_6$—Z and His—D$^\beta$Nal—Ala—Trp—DPhe—$A_6$—Z, and organic or inorganic addition salts thereof. Still more preferable are $A_0$—His—D$^\beta$Nal—Ala—Trp—DPhe—Lys—NH$_2$ (particularly, Ala—His—D$^\beta$Nal—Ala—Trp—DPhe—Lys—NH$_2$), and His—D$^\beta$Nal—Ala—Trp—DPhe—Lys—NH$_2$, and organic or inorganic addition salts of any of said polypeptides.

These compounds are typically easy to synthesize, have efficacy at promoting an increase in serum growth hormone levels, and are desirable for commercial scale production and utilization. In addition, these compounds may be advantageous in having physiochemical properties which are desirable for the efficient delivery of such polypeptide compounds to a wide variety of animal species because of the flexibility made possible by the various substitutions at numerous positions of the polypeptide compounds, by selecting the polar, neutral or non-polar nature of the N-terminal, C-terminal and center portions of these polypeptide compounds so as to be compatible with the desired method of delivery.

These D$^\beta$Nal$^2$ peptides typically show a higher level of potency at promoting the increase in serum growth hormone levels than most equivalent peptides with a different amino acid residue at the $A_2$ position.

His—D$^\beta$Nal—Ala—Trp—DPhe—Lys—NH$_2$ and $A_0$—His—D$^\beta$Nal—Ala—Trp—DPhe—Lys—NH$_2$ peptides such as Ala—His—D$^\beta$Nal—Ala—Trp—DPhe—Lys—NH$_2$, and organic or inorganic addition salts thereof are presently the most preferred.

These compounds have been shown to have a high level of potency at promoting the increase in serum growth hormone levels.

The compounds of this invention may be used to enhance blood GH levels in animals; enhance milk production in cows; enhance body growth in animals such as mammals (e.g., humans, sheep, bovines, and swine), as well as fish, fowl, other vertebrates and crustaceans; and increase wool and/or fur production in mammals. The amount of body growth is dependent upon the sex and age of the animal species, quantity and identity of the growth hormone releasing compound being administered, route of administration, and the like.

The novel polypeptide compounds of this invention can be synthesized according to the usual methods of solution and solid phase peptide chemistry, or by classical methods known in the art. The solid-phase synthesis is commenced from the C-terminal end of the peptide. A suitable starting material can be prepared, for instance, by attaching the required protected alpha-amino acid to a chloromethylated resin, a hydroxymethyl resin, a benzhydrylamine (BHA) resin, or a para-methyl-benzylhydrylamine (p-Me-BHA) resin. One such chloromethyl resin is sold under the tradename BIOBEADS SX-1 by Bio Rad Laboratories, Richmond, Calif. The preparation of the hydroxymethyl resin is described by Bodansky et al., Chem. Ind. (London) 38, 1597 (1966). The BHA resin has been described by Pietta and Marshall, Chem. Comm., 650 (1970) and is commercially available from Peninsula Laboratories, Inc., Belmont, Calif.

After the initial attachment, the alpha-amino protecting group can be removed by a choice of acidic reagents, including trifluoroacetic acid (TFA) or hydrochloric acid (HCl) solutions in organic solvents at room temperature. After removal of the alpha-amino protecting group, the remaining protected amino acids can be coupled stepwise in the desired order. Each protected amino acid can be generally reacted in about a 3-fold excess using an appropriate carboxyl group activator such as dicyclohexylcarbodiimide (DCC) or diisopropyl carbodiimide (DIC) in solution, for example, in methylene chloride (CH$_2$Cl$_2$) or dimethylformamide (DMF) and mixtures thereof.

After the desired amino acid sequence has been completed, the desired peptide can be cleaved from the resin support by treatment with a reagent such as hydrogen fluoride (HF) which not only cleaves the peptide from the resin, but also cleaves most commonly used side-chain protecting groups. When a chloromethyl resin or hydroxymethyl resin is used, HF treatment results in the formation of the free peptide acid. When the BHA or p-Me-BHA resin is used, HF treatment results directly in free peptide amides.

The solid-phase procedure discussed above is well known in the art and has been described by Stewart and Young, *Solid Phase Peptide Synthesis:* Second Edn. (Pierce Chemical Co., Rockford, Ill. 1984).

Some solution methods which can be employed to synthesize the peptide moieties of the instant invention are set forth in Bodansky et al., *Peptide Synthesis,* 2nd Edition, John Wiley & Sons, New York, N.Y. 1976.

It is believed that the peptides will be more preferably synthesized by a solution phase method which involves the condensation reaction of at least two peptide fragments.

This method comprises condensing a peptide fragment X—$A_1$—Y with the peptide fragment U-V-W, wherein all amino acid side-chains except for $A_1$ are neutral or protected, and wherein X is Prot. or Prot. —$A_0$, where Prot. is an N-terminus protecting group; Y is $A_2$—Q, Ala—$A_2$—Q, $A_2$—$A_3$—Q, Ala—$A_2$—$A_3$—Q, $A_2$—$A_3$—$A_4$—Q, Ala—$A_2$—$A_3$—$A_4$—Q, Ala—Q or —Q, where when Y is Q, U is J—$A_2$—$A_3$—$A_4$, or J—Ala—$A_2$—$A_3$—$A_4$. When Y is Ala—Q, U is J—$A_2$—$A_3$—$A_4$. When Y is $A_2$—Q or Ala—$A_2$—Q, U is J—$A_3$—$A_4$. When Y is $A_2$—$A_3$—Q or Ala—$A_2$—$A_3$—Q, U is J—$A_4$. When Y is $A_2$—$A_3$—$A_4$—Q or Ala—$A_2$—$A_3$—$A_4$—Q, U is J. V is $A_5$ or Z. When V is $A_5$, W is $A_6$—Z or Z. When V is Z, W is not present. $A_1$, $A_5$, $A_6$ and Z are as defined herein. In the present situation $A_2$ is $D^\beta Nal$ and $A_4$ is Trp.

Q is the carboxy terminus of a peptide fragment and is —$OR^3$ or —M, where M is a moiety capable of being displaced by a nitrogen-containing nucleophile and $R^3$ is H, an alkyl group containing one to about 10 carbon atoms, an aryl group having from 6 to about 12 carbon atoms or an arylalkyl group having from 7 to about 12 carbon atoms; J represents the amine terminus of the indicated fragment and is H or a protecting group, which does not hinder the coupling reaction, for example, benzyl.

Thereafter, one removes the protecting groups. Alternatively, one may use the protected peptide thus formed in further condensations to prepare a larger peptide.

This preferred method is more fully described in U.S. patent application Ser. No. 558,121 filed on Jul. 24, 1990, concurrently with this application, by John C. Hubbs and S. W. Parker entitled "Process for Synthesizing Peptides", published as WO 92/10709, which is incorporated herein by reference.

In accordance with another embodiment of the present invention, a method is provided for promoting release and/or elevation of growth hormone levels in the blood of an animal. Said method comprises administering to an animal an effective dose of at least one of the above-described polypeptides.

The compounds of this invention can be administered by oral, parenteral (intramuscular (i. m.), intraperitoneal (i. p.), intravenous (i. v.) or subcutaneous (s. c.) injection), nasal, vaginal, rectal or sublingual routes of administration and can be formulated in dose forms appropriate for each route of administration. Parenteral administration is preferred.

Solid dose forms for oral administration include capsules, tablets, pills, powders and granules. In such solid dose forms, the active compound is mixed with at least one inert carrier such as sucrose, lactose, or starch. Such dose forms can also comprise, as is normal practice, additional substances other than inert diluents, e.g., lubricating agents such as magnesium stearate. In the case of capsules, tablets and pills, the dose forms may also comprise buffering agents. Tablets and pills can additionally be prepared with enteric coatings.

Liquid dose forms for oral administration include emulsions, solutions, suspensions, syrups, the elixirs containing inert diluents commonly used in the art, such as water. Besides, such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dose forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in a medium of sterile water, or some other sterile injectable medium immediately before use.

The novel compounds of the present invention are also useful when administered in combination with growth hormone releasing hormone (i.e., naturally occurring growth hormone releasing hormone, analogs and functional equivalents thereof), as well as in combination with other compounds which promote the release of growth hormone, e.g., growth hormone releasing peptides (see U.S. Pat. No. 4,880, 778 which is incorporated herein by reference U.S. Pat. No. 4,880,778 states at col. 3, line 11-col. 5, line 8:

In accordance with the broadest scope of the present invention, the term "Group 1 polypeptides" is intended to include naturally occurring growth hormone releasing hormones, e.g., human, porcine, bovine, ovine and rat growth hormone releasing hormones, such as compounds #144– 149 below, and functional analogs thereof. Such peptides act at the growth hormone releasing hormone receptor of mammals and other vertebrates, crustaceans and the like, to cause the release of growth hormone. Representative peptides included within this definition are selected from any of the polypeptides:

(a) having the following amino acid sequences in positions 1–44 (numbered from N terminus to C terminus):
(#144)  YADAIFTNSYRKVLGQLSARKLLQDIM-SRQQGESNQERGARARL-X,
(#145)  YADAIFTNSYRKVLGQLSARKLLQDIM-SRQQGERNQEQGARVRL- X,
(#146)  YADAIFTNSYRKVLGQLSARKLLQDIMN-RQQGERNQEQGAKVRL-X,
(#148)  YADAIFTNSYRKILGQLSARKLLQDIMN-RQQGERNQEQGAKVRL-X, and
(#149)  HADAIFTSSYRRILGQLYARKLLHEIMN-RQQGERNQEQRSRFN-X;

wherein the C-terminal amino acid has the following truncated general formula

wherein each R¹ independently represents the substituents of the particular amino acid residue, e.g., hydrogen, alkyl, aryl, amino or acid substituents; X denotes the C terminal end group and is selected from —CONH₂, —COOH, —COOR, —CONRR, —CH₂OH, and —CH₂OR, wherein R is an alkyl group having 1–6 carbon atoms or an aromatic ring having up to 12 carbon atoms; and wherein the amino acid residue abbreviations used are in accordance with the standard peptide nomenclature:

G=Gly (Glycine)
Y=Tyr (L-Tyrosine)
I=Ile (L-Isoleucine)
E=Glu (L-Glutamic Acid)
T=Thr (L-Threonine)
F=Phe (L-Phenylalanine)
A=Ala (L-Alanine)
K=Lys (L-Lysine)
D=Asp (L-Aspartic Acid)
C=Cys (L-Cysteine)
R=Arg (L-Arginine)
Q=Gln (L-Glutamine)
P=Pro (L-Proline)
L=Leu (L-Leucine)
M=Met (L-Methionine)
S=Ser (L-Serine)
N=Asn (L-Asparagine)
H=His (L-Histidine)
W=Trp (L-Tryptophan)
V=Val (L-Valine)

wherein all three letter amino acid abbreviations preveded by a "D" indicate the D-configuration of the amino acid residue.

While essentially steriochemically pure D or L amino acids are referred to throughout this specification, it is to be understood that mixtures of the D/L stereoisomers of the amino acid residues are also operable, while sometimes having a reduced level of biological activity as a function of the relative amount of the unspecified configuration which is present. Additional amino acid and peptide abbreviations which appear throughout the specification include:

Abu: alpha-Aminobutyric Acid
Aib: alpha-Aminoisobutyric acid
Arg:(NO₂): Ng-Nitro-L-Arginine
(beta)Ala: beta-Alanine (i.e., 3-Amino Propanoic Acid)
Dab: 2,4-Diaminobutyric Acid
DOPA: 3,4-Dihydroxyphenylalanine
Gly-ol: 2-Aminoethanol
Hyp: trans-4-Hydroxy-L-Proline
Met(O): Methionine sulfoxide
Met(O)-ol: Methionine sulfoxide alcohol
Nle: L-Norleucine
Pal: 3-Pyridyl Alanine
Pgl: Phenylglycine
Sar: Sarcosine
Sar-ol: Sarcosine alcohol
Thz: L-Thiazolidine-4-carboxylic acid Either:
The Dermorphins: Tyr—DAla—Phe—Gly—Tyr—pro—Ser—NH₂ (#8801) or Tyr—DAla—Phe—Gly—Tyr—Hyp—Ser—NH₂ (#8802)

(b) any one of said (a) polypeptides having the following amino acid substitutions:
position 1 of (#144–#148) is DTyr or His;
position 1 of (#149) is Tyr or DHis;
position 2 of (#144–149) is (NMe)DAla or Aib or DAla;
position 3 of (#144–149) is DAsp;
position 4 of (#144–149) is DAla; and
position 1+2 of (#144–#149) is;
DTyr¹+ DAla², DTyr¹+(NMe)DAla², or DTyr¹ +Aib²;

(c) any one of said (a) or (b) polypeptides having a substitution of Nle for Met at position 27;

(d) any one of said (a), (b) or (c) polypeptides in which the N-terminus —NH₂ is replaced by —NHCOR and wherein R is an alkyl group having 1 to 6 carbon atoms, or an aromatic ring having up to 12 carbon atoms;

(e) fragments of any one of said (a), (b), (c) or (d) polypeptides which contain at least the amino acid residues of positions 1–29;

(f) having the following specific amino acid sequences in positions 1–29 (numbered from N terminus to C terminus):
YADAIFTNSYRKVLQQLLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X, (linear dithiol),and
YADAIFTNCYRKVLCQLSARKLLQDIMSR-X (cyclic disulfide);
wherein the C-terminal amino acid and X are as defined above; and modification of anyone of these group (f) compounds in accordance with the modifications set forth in (b), (c) and (d) above; and (g) organic or inorganic addition salts of any of said (a), (b), (c), (d), (e) or (f) polypeptides of Group 1.

And at col. 5, line 43-col. 6, line 22:

Group 3 polypeptides contemplated within the broad scope of the present invention are selected from any of the polypeptides having the structure:

Tyr—DArg—Phe—NH₂;
Tyr—DAla—Phe—NH₂;
Tyr—DArg(NO₂)—Phe—NH₂;
Tyr—DMet(O)—Phe—NH₂;
Tyr—DAla—Phe—Gly—NH₂;
Tyr—DArg—Phe—Gly—NH₂;
Tyr—DThr—Phe—Gly—NH₂;
Phe—DArg—Phe—Gly—NH₂;
Tyr—DArg—Phe—Sar;
Tyr—DAla—Gly—Phe—NH₂;
Tyr—DArg—Gly—Trp—NH₂;
Tyr—DArg (NO₂)—Phe—Gly—NH₂;
Tyr—DMet (O)—Phe—Gly—NH₂;
(NMe) Tyr—DArg—Phe—Sar—NH₂;
Tyr—DArg—Phe—Gly—ol;
Tyr—DArg—Gly—(NMe)Phe—NH₂;
Tyr—DArg—Phe—Sar—ol
Tyr—DAla—Phe—Sar—ol
Tyr—DAla—Phe—Gly—Tyr—NH₂;
Gly—Tyr—DArg—Phe—Gly—NH₂;
Tyr—DThr—Gly—Phe—Thz—NH₂;
Gly—Tyr—DAla—Phe—Gly—NH₂;
Tyr—DAla—Phe—Gly—ol;
Tyr—DAla—Gly— (NMe) Phe—Gly—ol;
Tyr—DArg—Phe—Sar—NH₂;
Tyr—DAla—Phe—Sar—NH₂;

Tyr—DAla—Phe—Sar;
Tyr—DAla—Gly—(NMe) Phe—NH$_2$;
Sar—Tyr—DArg—Phe— Sar—NH$_2$;
Tyr—DCys —Phe—Gly—DCys —NH$_2$ (cyclic disulfide);
Tyr—DCys —Phe—Gly—DCys—NH$_2$ (free dithiol);
Tyr—DCys—Gly—Phe—DCys —NH$_2$ (cyclic disulfide);
Tyr—DCys—Gly—Phe—DCys (free dithiol);
Tyr—DAla—Phe—Gly—Tyr —Pro— Ser—NH$_2$;
Tyr—DAla—Phe —Sar—Tyr—Pro—Ser—NH$_2$;
Tyr—DAla—Phe—Sar—Phe—Pro—Ser—NH$_2$;
Tyr —DAla —Phe—Gly—Tyr—Hyp—Ser—NH$_2$;
Tyr—DAla—Phe—Sar—Tyr—Hyp—Ser—NH$_2$;
Tyr—DAla—Phe—Sar—Phe—Hyp—Ser—NH$_2$;
Tyr —DArg—Phe—Gly—Tyr—Hyp—Ser—NH$_2$;
Tyr—DArg—Phe—Sar—Tyr—Pro—Ser—NH$_2$;
Tyr—DArg—Phe—Sar—Tyr—Hyp—Ser—NH$_2$;
Tyr—DArg—Phe—Gly—Tyr—Pro—Ser—NH$_2$; and
organic or inorganic addition salts of any of said polypeptides of Group 3.

And at col. 6, line 30-col. 7, line 27:

In accordance with this preferred embodiment of the present invention, the term "Group 1 polypeptides" is intended to include naturally occurring growth hormones, e.g., human, porcine, bovine, ovine and rat growth hormone releasing hormones, such as compounds #144–149 below, and functional analogs thereof, which polypeptides act at the growth hormone releasing hormone receptor of mammals and other vertebrates. Compounds within this definition are selected from any of the polypeptides:

(a) having the following amino acid sequences in positions 1– 44 (numbered from N terminus to c terminus):
(#144) YADAIFTNSYRKVLGQLSARKLLQDIMSRQQGESNQERGARARL—CONH$_2$ (hGHRH),
(#145) YADAIFTNSYRKVLGQLSARKLLQDIMSRQQGERNQEQGARVRL—CONH$_2$ (pGHRH),
(#146) YADAIFTNSYRKVLGQLSARKLLQDIMNRQQGERNQEQGAKVRL—CONH$_2$ (bGHRH),
(#148) YADAIFTNSYRKILGQLSARKLLQDIMNRQQGERNQEQGAKVRL—CONH$_2$ (oGHRH), and
(#149) HADAIFTSSYRRILGQLYARKLLHEIMNRQQGERNQEQRSRFN—COOH wherein the single letter abbreviation for the amino acid residues are as previously defined including the previous definition for the C-terminal amino acid residues;

(b) any one of said (a) polypeptides having the following amino acid substitutions;
position 1 of (#144–148) is DTyr or His;
position 1 of (#149) is Tyr;
position 2 of (#144–#149) is (NMe)Dala or Aib or DAla;
position 3 of (#144–#149) is DAsp;
position 4 of (#144–149) is DAla;
position 1+2 of (#144–149) is DTyr$^1$ + DAla$^2$;

(c) any of said (a) or (b) polypeptides having a substitution of the Nle for Met at position 27;

(d) any one of said (a), (b), or (c) polypeptides in which the N-terminus —NH$_2$ is replaced by —NHCOCH$_3$;

(e) fragments of any one of said (a), (b), (c) or (d) polypeptides which contain at least the amino acid residues of positions 1–29, (f) having the following amino acid sequences in positions 1– 29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLIARKLLQDIMQR-X,
YADAIFSSAYRRLLAQLASRRLLQELLAR-X,
YADAIFTNCYRKVLCQLSARKLLQDIMSR-X (linear dithiol), and
YADAIFTNCYRKVLCQLSARKLLQDIMSR-X (cyclic disulfide);

wherein the C-terminal amino acid and X are as defined above; and modification of any of these group (f) compounds in accordance with the modifications set forth in (b), (c) and (d) above; and (g) organic or inorganic addition Salts of any of said (a), (b), (c), (d), (e) or (f) polypeptides of Group 1). Such combinations represent an especially preferred means to administer the growth hormone releasing peptides of the present invention because the combination promotes the release of much more growth hormone than is predicted by the summation of the individual responses for each component of the combination, i.e., the combination provides a synergistic response relative to the individual component. Further details on the administration of combinations of growth hormone releasing peptides are described in the above-cited patent. Such synergistic compounds are preferably compounds which act as an agonist at the growth hormone releasing hormone receptor or inhibit the effect of somatostatin. The synergism can be binary, i.e. the present compound and one of the synergistic compounds, or involve more than one synergistic compound.

The amount of polypeptide or combination of polypeptides of the present invention administered will vary depending on numerous factors, e.g., the particular animal treated, its age and sex, the desired therapeutic affect, the route of administration and which polypeptide or combination of polypeptides are employed. In all instances, however, a dose effective to promote release and elevation of growth hormone level in the blood of the recipient animal is used. Ordinarily, this dose level falls in the range of between about 0.1 e.g., to 10 mg of total polypeptide per kg of body weight. The preferred amount can readily be determined empirically by the skilled artisan based upon the present disclosure.

For example, in humans when the mode of administration is i. v. the preferred dose level falls in the range of about 0.1 μg to 10 μg of total polypeptide per kg of body weight, more preferably, about 0.5 μg to 5 μg of total polypeptide per kg of body weight, still more preferably about 0.7 μg about 3.0 μg per kg of body weight. When combinations of growth hormone releasing peptides are used, lower amounts of the presently described peptide can be used. For example, combining the presently described peptide with, for example, a synergistic compound in Group 1 of U.S. Pat. No. 4,880,778 such as GHRH, a preferred range is about 0.1 μg to about 5 μg of the presently described compound (e.g., Ala—His—D$^\beta$Nal—Ala—Trp—DPhe—A$_6$—Z or His—D$^\beta$Nal—Ala—Trp—DPhe—A$_6$—Z) per kg of body weight and about 0.5 μg to about 15.0 μg of synergistic compound (e.g., GHRH) and more preferably about 0.1 μg to about 3 μg of the present compound with about 1.0 μg to about 3.0 μg of the synergistic compound per kg of body weight.

When the mode of administration is oral, greater amounts are typically needed. For example, in humans for oral administration, the dose level is typically about 30 μg to about 600 μg of polypeptide per kg of body weight, more preferably about 70 μg to about 500 μg of polypeptide per kg of body weight, still more preferably, about 100 μg to about 350 μg of total polypeptide per kg of body weight, even more preferably, about 200 μg to about 300 μg of total polypeptide per kg of body weight. Cows require about the same dose level as humans, while rats typically require higher dose levels. The exact level can readily be determined empirically based upon the present disclosure.

In general, as aforesaid, the administration of combinations of growth hormone releasing peptides will allow for lower doses of the individual growth hormone releasing compounds to be employed relative to the dose levels required for individual growth hormone releasing compounds in order to obtain a similar response, due to the synergistic effect of the combination.

Also included within the scope of the present invention are compositions comprising, as an active ingredient, the organic and inorganic addition salts of the above-described polypeptides and combinations thereof; optionally, in association with a carrier, diluent, slow release matrix, or coating.

The organic or inorganic addition salts of the growth hormone releasing compounds and combinations thereof contemplated to be within the scope of the present invention include salts of such organic moieties as acetate, trifluoroacetate, oxalate, valerate, oleate, laurate, benzoate, lactate, tosylate, titrate, maleate, fumarate, succinate, tartrate, naphthalate, and the like; and such inorganic moieties as Group I (i.e., alkali metal salts), Group II (i.e. alkaline earth metal salts) ammonium and protamine salts, zinc, iron, and the like with counterions such as chloride, bromide, sulfate, phosphate and the like, as well as the organic moieties referred to above.

Pharmaceutically acceptable salts are preferred when administration to human subjects is contemplated. Such salts include the non-toxic alkali metal, alkaline earth metal and ammonium salts commonly used in the pharmaceutical industry including sodium, potassium, lithium, calcium, magnesium, barium, ammonium and protamine salts which are prepared by methods well known in the art. The term also includes non-toxic acid addition salts which are generally prepared by reacting the compounds of this invention with a suitable organic or inorganic acid. Representative salts include hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napthylate, and the like.

The invention will be further illustrated by the following non-limiting examples.

EXAMPLE 1

Synthesis of the Growth Hormone Releasing Peptides

Paramethyl benzhydrylamine hydrochloride (pMe—BHA—HCl) resin is placed in a reaction vessel on a commercially available automated peptide synthesizer. The resin is substituted with free amine up to a loading of about 5 mmoles per gram. The compounds are prepared by coupling individual amino acids starting at the carboxy terminus of the peptide sequence using an appropriate activating agent, such as N,N'—dicyclohexylcarbodiimide (DCC). The alpha amine of individual amino acids are protected, for example, as the t-butyloxycarbonyl derivative (t—Boc) and the reactive side chain functionalities are protected as outlined in Table 1.

TABLE 1

Side Chain Protecting Groups Suitable For Solid Phase Peptide Synthesis

| Amino Acid | Protecting Group |
|---|---|
| Arginine: | $N^g$-Tosyl |
| Aspartic Acid: | O-Benzyl |
| Cysteine: | S-para-Methylbenzyl |
| Glutamic Acid: | O-Benzyl |
| Histidine: | $N^{im}$-Tosyl |
| Lysine: | $N^\epsilon$-2,4-Dichlorobenzyloxycarbonyl |
| Methionine: | S-Sulfoxide |
| Serine: | O-Benzyl |
| Threonine: | O-Benzyl |
| Tryptophan: | $N^{in}$-Formyl |
| Tyrosine: | O-2,6-Dichlorobenzyl |

Prior to incorporation of the initial amino acid, the resin is agitated three times (about one minute each) with dichloromethane ($CH_2Cl_2$; about 10 mL/gm of resin), neutralized with three agitations (about two minutes each) of N,N—diisopropylethylamine (DIEA) in dichloromethane (10:90; about 10 mL/gm of resin) and agitated three times (about one minute each) with dichloromethane (about 10 mL/gm of resin). The initial and each of the subsequent amino acids are coupled to the resin using a preformed symmetrical anhydride using about 3.0 times the total amount of the binding capacity of the resin of a suitably protected amino acid and about 1.5 times the total amount of the binding capacity of the resin of DCC in an appropriate amount of dichloromethane. For amino acids with a low dichloromethane solubility, N,N—dimethylformamide (DMF) is added to achieve a homogenous solution. Generally, the symmetrical anhydride is prepared up to 30 minutes prior to introduction into the reaction vessel at room temperature or below. The dicyclohexylurea that forms upon preparation of the symmetrical anhydride is removed via gravity filtration of the solution into the reaction vessel. Progress of the coupling of the amino acid to the resin is commonly monitored via a color test using a reagent such as ninhydrin (which reacts with primary and secondary amines). Upon complete coupling of the protected amino acid to the resin (>99%), the alpha amine protecting group is removed by treatment with acidic reagent(s). A commonly used reagent consists of a solution of trifluoroacetic acid (TFA), and anisole in dichloromethane (45:2:53). The complete procedure for incorporation of each individual amino acid residue onto the resin is outlined in Table 2.

TABLE 2

Procedure for Incorporation Of Individual Amino Acids Onto a Resin

| | Reagent | Agitations | Time/Agitation |
|---|---|---|---|
| 1. | Dichloromethane | 3 | 1 min. |
| 2. | TFA, Anisole, Dichloromethane (45:2:53) | 1 | 2 min. |
| 3. | TFA, Anisole, Dichloromethane (45:2:53) | 1 | 20 min. |
| 4. | Dichloromethane | 3 | 1 min. |
| 5. | DIEA, Dichloromethane (10:90) | 3 | 2 min. |
| 6. | Dichloromethane | 3 | 1 min. |
| 7. | Preformed symmetrical anhydride | 1 | 15–120 min.* |
| 8. | Dichloromethane | 3 | 1 min. |
| 9. | iso-Propanol | 3 | 1 min. |
| 10. | Dichloromethane | 3 | 1 min. |
| 11. | Monitor progress of the | | |

TABLE 2-continued

Procedure for Incorporation Of Individual Amino Acids Onto a Resin

| Reagent | Agitations | Time/Agitation |
|---|---|---|
| coupling reaction** | | |
| 12. Repeat steps 1–12 for each individual amino acid | | |

*Coupling time depends upon the individual amino acid.
**The extent of coupling can be generally monitored by a color test. If the coupling is incomplete, the same amino acid can be recoupled by repeating steps 7–11. If the coupling is complete the next amino acid can be coupled.

By employing this method of peptide synthesis, novel resin-bound polypeptides such as:

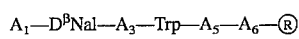

are obtained (wherein $A_1$, $A_3$, $A_5$, and $A_6$ are as defined above, and Ⓡ is a polymeric resin and the functional groups of the constituent amino acids are protected with suitable protecting groups as needed). Specific sequences (in appropriately protected form) which have been prepared include:
His—D$^\beta$Nal—Ala—Trp—DPhe—Lys—Ⓡ,
Ala—His—D$^\beta$Nal—Ala—Trp—DPhe—Lys—Ⓡ,
Ala—His—DTrp—Ala—Trp—DPhe—Lys—Ⓡ,
His—Ala—DTrp—Ala—Trp—DPhe—Lys—Ⓡ,
His—D$^\alpha$Nal—Ala—Trp—DPhe—Lys—Ⓡ,
His—DAsp—Ala—Trp—DPhe—Lys—Ⓡ,
His—DCys(SMe)—Ala—Trp—DPhe—Lys—Ⓡ,
His—DTrp—Ala—Trp—DPhe—Ala—Lys—Ⓡ,
His—D$^\beta$Nal—Ala—Trp—DPhe—Ala—Lys—Ⓡ,
Ala—His—D$^\beta$Nal—Ala—Trp—DPhe—Ala—Lys—Ⓡ,
Try—DArg—Phe—Gly—Ⓡ.

EXAMPLE 2

In Vivo GH Release in Rats

Immature female Sprague-Dawley rats were obtained from the Charles River Laboratories (Wilmington, Mass.). After arrival they were housed at 25° C. with a 14:10 hour light:dark cycle. Water and Purina rat chow were available ad libitum. Pups were kept with their mothers until 21 days of age.

Twenty-six day old rats, six rats per treatment group, were anesthetized interperitoneally with 50 mg/Kg of pentobarbital 20 minutes prior to i. v. treatment with peptide. Normal saline with 0.1% gelatin was the vehicle for intravenous (i. v.) injections of the peptides. The anesthetized rats, weighing 55–65 grams, were injected i. v. with the quantity of growth hormone releasing compounds indicated in Tables 3 and 4. Injection was made as a 0.2 mL solution into the jugular vein.

All animals were sacrificed by guillotine 10 minutes after the final test injection (see Tables 3 and 4). Trunk blood for the determination of blood GH levels was collected following decapitation. After allowing the blood to clot, it was centrifuged and the serum was separated from the clot. Serum was kept frozen until the day of sampling for radioimmunasay (RIA) determination of growth hormone levels according to the following procedure, as developed by the National Institute of Arthritis, Diabetes and Digestive and Kidney Diseases (NIADDK).

Reagents are generally added to the RIA analysis tubes at a single sitting, at refrigerator temperature (about 4° C.) in the following sequence:

(a) buffer, (b) "cold" (i.e., non-radioactive) standard or unknown serum sample to be analyzed, (c) radio-iodinated growth hormone antigen, and (d) growth hormone antiserum.

Reagent addition is generally carried out so that there is achieved a final RIA tube dilution of about 1:30,000 (antiserum to total liquid volume; vol:vol).

The mixed reagents are then typically incubated at room temperature (about 25° C.) for about 24 hours prior to addition of a second antibody (e.g., goat or rabbit antimonkey gamma globulin serum) which binds to and causes precipitation of the complexed growth hormone antiserum. Precipitated contents of the RIA tubes are then analyzed for the number of counts in a specified period of time in a gamma scintillation counter. A standard curve is prepared by plotting number of radioactive counts versus growth hormone (GH) level. GH levels of unknowns are then determined by reference to the standard curve.

Serum GH was measured by RIA with reagents provided by the National Hormone and Pituitary Program.

Serum levels in Tables 3 and 4 are recorded in ng/mL in terms of the rat GH standard of 0.61 International Units/mg (IU/mg). Data is recorded as the mean +/− standard error of the mean (SEM). Statistical analysis was performed with Student's t-test. NS means the difference was not statistically significant. In Tables 3 and 4 the results shown are the average of studies with six rats.

TABLE 3

In Vivo GH Release (ng/mL) Promoted By Growth Hormone Releasing Compounds In Pentobarbital Anesthetized Rats (Animals Sacrificed 10 Minutes After Final Injection)

| Column A Growth Hormone Releasing Compounds | Total Dose (μg) | Control GH ng/mL | GH Released by Compound in Column A ng/mL + SEM | p value |
|---|---|---|---|---|
| His—DTrp—Ala—Trp— | .1 | 151 ± 16 | 246 ± 39 | — |
| DPhe—Lys—NH$_2$ | .3 | 151 ± 16 | 670 ± 75 | — |
| | 1.0 | 151 ± 16 | 1000 ± 276 | — |
| | 3.0 | 151 ± 16 | 2106 ± 216 | — |
| His—D$^\beta$Nal—Ala— | .1 | 151 ± 16 | 938 ± 255 | <.02 |
| Trp—DPhe—Lys—NH$_2$— | .3 | 151 ± 16 | 1716 ± 258 | <.02 |

TABLE 3-continued

In Vivo GH Release (ng/mL) Promoted By Growth
Hormone Releasing Compounds In Pentobarbital Anesthetized Rats
(Animals Sacrificed 10 Minutes After Final Injection)

| Column A Growth Hormone Releasing Compounds | Total Dose (μg) | Control GH ng/mL | GH Released by Compound in Column A ng/mL + SEM | p value |
|---|---|---|---|---|
| | 1.0 | 151 ± 16 | 3728 ± 691 | <.01 |
| | 3.0 | 151 ± 16 | 3238 ± 273 | <.01 |
| His—DTrp—Ala—Trp—Dphe—Lys—NH$_2$ | .1 | 138 ± 12 | 226 ± 31 | — |
| | .3 | 138 ± 12 | 613 ± 73 | — |
| | 1.0 | 138 ± 12 | 1581 ± 228 | — |
| | 3.0 | 138 ± 12 | 2875 ± 393 | — |
| Ala—His—DTrp—Ala—Trp—DPhe—Lys—NH$_2$ | .1 | 138 ± 12 | 254 ± 78 | NS — |
| | .3 | 138 ± 12 | 809 ± 59 | NS — |
| | 1.0 | 138 ± 12 | 1516 ± 215 | NS — |
| | 3.0 | 138 ± 12 | 3095 ± 473 | NS — |
| Ala—His—D$^\beta$Nal—Ala—Trp—DPhe—Lys—NH$_2$ | .1 | 138 ± 12 | 1128 ± 309 | <.02 <.02 |
| | .3 | 138 ± 12 | 2479 ± 389 | <.001–.001 |
| | 1.0 | 138 ± 12 | 3899 ± 514 | –.001–.001 |
| | 3.0 | 138 ± 12 | 4202 ± 369 | <.05 NS |
| Ala—His—DTrp—Ala—Trp—DPhe—Lys—NH$_2$ | 0.1 | 111 ± 25 | 360 ± 35 | — |
| | 0.3 | 111 ± 25 | 903 ± 217 | — |
| | 1.0 | 111 ± 25 | 2957 ± 427 | — |
| | 3.0 | 111 ± 25 | 3956 ± 485 | — |
| Ala—His—D$^\beta$Nal—Ala—Trp—DPhe—Lys—NH$_2$ | 0.1 | 111 ± 25 | 970 ± 169 | <.01 |
| | 0.3 | 111 ± 25 | 2898 ± 247 | <.001 |
| | 1.0 | 111 ± 25 | 3908 ± 327 | NS |

TABLE 4

| Peptide | Total (μg) Dose | Control GH ng/mL | GH Released ng/mL |
|---|---|---|---|
| His—DAsp—Ala—Trp—DPhe—Lys—NH$_2$ | 1.0 | 150 ± 20 | 154 ± 63 |
| | 3.0 | 150 ± 20 | 155 ± 34 |
| | 10.0 | 150 ± 20 | 163 ± 44 |
| | 30.0 | 150 ± 20 | 224 ± 62 |
| | 100.0 | 150 ± 20 | 178 ± 83 |
| His—DCys(SMe)—Ala—Trp—DPhe—Lys—NH$_2$ | .3 | 181 ± 69 | 178 ± 28 |
| | 1.0 | 181 ± 69 | 193 ± 28 |
| | 3.0 | 181 ± 69 | 180 ± 34 |
| His—D$^\alpha$Nal—Ala—Trp—DPhe—Lys—NH$_2$ | .1 | 151 ± 16 | 280 ± 70 |
| | .3 | 151 ± 16 | 439 ± 122 |
| | 1.0 | 151 ± 16 | 1130 ± 179 |
| | 3.0 | 151 ± 16 | 2319 ± 139 |
| His—DTrp—Ala—Trp—DPhe—Lys—NH$_2$ | .1 | 181 ± 69 | 512 ± 43 |
| | .3 | 181 ± 69 | 566 ± 114 |
| | 1.0 | 181 ± 69 | 1531 ± 303 |
| | 3.0 | 181 ± 69 | 2349 ± 267 |
| His—DTrp—Ala—Trp—DPhe—Ala—Lys—NH$_2$ | .1 | | 420 ± 105 |
| | .3 | | 900 ± 163 |
| | 1.0 | | 1965 ± 366 |
| | 3.0 | | 4553 ± 670 |
| His—D$^\beta$Nal—Ala—Trp—DPhe—Ala—Lys—NH$_2$ | .1 | | 484 ± 89 |
| | .3 | | 971 ± 241 |
| | 1.0 | | 1593 ± 359 |
| | 3.0 | | 3337 ± 583 |
| His—Ala—D$^\beta$Nal—Ala—Trp—DPhe—Ala—Lys NH$_2$ | .1 | | 94 ± 18 |
| | .3 | | 292 ± 55 |
| | 1.0 | | 694 ± 131 |
| | 3.0 | | 1440 ± 407 |
| His—Ala—DTrp—Ala—Trp—DPhe—Lys—NH$_2$ | .1 | | — |
| | .3 | | 261 ± 32 |
| | 1.0 | | 830 ± 103 |
| | 3.0 | | 2588 ± 341 |

Tables 3 and 4 show that compounds of the invention promote the release and elevation of growth hormone levels in the blood of rats to which such compounds have been administered. These tables also show that His—D$^\beta$Nal—Ala—Trp—DPhe—Lys—NH$_2$ is more active than compounds having DTrp, D$^\alpha$Nal, DAsp, and DCys (SMe) in the A$_2$ position. Similarly, Ala—His—D$^\beta$Nal—Ala—Trp—DPhe—Lys—NH$_2$ is more active than the equivalent DTrp compound.

EXAMPLE 3

Administration of a Combination of GH-Releasing Compounds

The procedure of Example 2 was repeated, except the rats were not anesthetized nor were they pretreated with pentobarbital, and a combination of peptides were administered to the rats. The compounds administered, the dose level and results are set forth in Table 5.

TABLE 5

In Vivo Synergistic Effects In
Unanesthetized Rats Of Invention Compound With
Group 1 and/or Group 3 Compounds

| Compound Administered | | | Dose (μg) | GH Released (ng/mL) ±SEM |
|---|---|---|---|---|
| Control | — | — | — | 12 ± 3 |
| 175-1[a] | — | — | 1 | 58 ± 13 |
| 175-1 | — | — | 3 | 240 ± 32 |
| C[b] | — | — | 10 | 204 ± 50 |
| GHRH[c] | — | — | 3 | 131 ± 50 |
| TP[d] | — | — | 10 | 79 ± 29 |
| 175-1 | GHRH | — | 1 + 3 | 2014 ± 224 |
| 175-1 | TP | — | 1 + 10 | 987 ± 204 |
| 175-1 | GHRH | TP | 1 + 3 + 10 | 4150 ± 555 |
| 175-1 | GHRH | — | 3 + 3 | 1994 ± 249 |
| 175-1 | TP | — | 3 + 10 | 2149 ± 451 |
| 175-1 | GHRH | TP | 3 + 3 + 10 | 2922 ± 384 |
| C | GHRH | — | 10 + 3 | 2525 ± 453 |
| C | TP | — | 10 + 10 | 1597 ± 387 |
| C | GHRH | TP | 10 + 3 + 10 | 4344 ± 374 |

*Groups 1 and 3 compounds are described in detail in U.S. Pat. No. 4,880,778.
[a]175-1 = His—D$^\beta$Nal—Ala—Trp—DPhe—Lys—NH$_2$ (Compound within invention)

TABLE 5-continued

In Vivo Synergistic Effects In Unanesthetized Rats Of Invention Compound With Group 1 and/or Group 3 Compounds

| Compound Administered | Dose (μg) | GH Released (ng/mL) |
|---|---|---|

[b]C = His—DTrp—Ala—Trp—DPhe—Lys—NH$_2$ (Comparison compound)
[c]GHRH = Tyr—Ala—Asp—Ala—Ile—Phe—Thr—Asn—Ser—Tyr—Arg—Lys—Val—Leu—Gly—Gln—Leu—Ser—Ala—Arg—Lys—Leu—Leu—Gln—Asp—Ile—Nle—Ser—Arg—NH$_2$ (Group 1 Compound)
[d]TP = Tyr—DArg—Phe—Gly—NH$_2$ (Group 3 Compound)

Table 5 shows that the invention compound display a synergistic response when administered with exemplary Group 1 and/or Group 3 compounds. The results in Table 5 further show that the invention compound has a greater synergistic response that that obtained with a comparison compound (C), which has previously been shown to have a synergistic response.

EXAMPLE 4

Condensation Reaction of Peptide Fragments to Form Peptide

General Procedures

Melting points can be determined using a Thomas Hoover capillary melting point apparatus. Infrared (IR) spectra can be recorded on a Perkin-Elmer Model 137 or a Nicolet Model 5DX spectrophotometer and reported in wave numbers (cm$^{-1}$). Mass spectra (MS) can be obtained using a VG Analytical Ltd. Model ZAB-1F Mass Spectrometer in EI (electron impact), FD (field desorption) or FAB (fast atom bombardment) modes. GCMS can be obtained using a Finnigan 4023 GCMS equipped with a 30 m DB5 capillary column (J & W Scientific) using helium carrier gas. Optical rotations can be measured using an Autopol III polarimeter manufactured by Rudolph Research.

$^1$H NMR spectra can be obtained on a JEOL GX-400 NMR instrument operating at 400 MHz or a JEOL GX-270 NMR instrument operating at 270 MHz. These instruments are capable of a routine digital resolution of less than 0.7 Hz. Chemical shifts are expressed in parts per million relative to internal 3—(trimethylsilyl)—tetradeutero sodium propionate (TSP).

High performance liquid chromatography (HPLC) can be accomplished using a Hitachi system consisting of a L-5000 gradient controller and a 655A pump attached to a Vydac 201TP1010 or 218TP1010 semipreparative column. Combinations of water containing 0.2% trifluoroacetic acid and methanol can be used as the eluting solvent. Typically, compounds of interest will be eluted at a flow rate of six mL per minute with a gradient increasing the organic component at a rate of approximately 1–2% per minute. Compounds are then detected at appropriate wavelengths using an LKB 2140 diode array U. V. detector. Integrations can then be accomplished using Nelson Analytical software (Version 3.6).

Reactions will be carried out under an inert atmosphere of nitrogen or argon unless otherwise specified. Anhydrous tetrahydrofuran (THF, U. V. grade) and dimethylformamide (DMF) can be purchased from Burdick and Jackson and used directly from the bottle.

A. Preparation of Tripeptide Fragment—HN—Trp—DPhe—Lys—(Boc)—NH$_2$
$N^\alpha$—Benzyloxycarbonyl—($N^\epsilon$—t—butoxycarbonyl)lysine amide, 4.

To a 10° C. solution of carbonyldiimidazole (CDI, 2, 88.24 g, 0.544 mol) and dry tetrahydrofuran (THF, 1500 mL), $N^\alpha$—benzyloxycarbonyl—($N^\epsilon$—t—butoxycarbonyl)lysine(1, 180 g, 0.474 mol), are slowly added. Gas evolution is observed during this addition. While the $N^\epsilon$—benzyloxycarbonyl—($N^\epsilon$—t—butoxycarbonyl)lysine imidazolide intermediate, 3, is forming, a saturated solution of ammonia and THF (2000 mL) is prepared (anhyd. NH$_3$ gas is passed through THF at 5°–10° C.). After formation of intermediate 3 is judged to be complete (when gas evolution has ceased, approximately 2 hours), one-half of the THF solution containing 3 is added to the ammonia solution. The remainder of the solution containing 3 is added 30 minutes later. A continuous flow of ammonia gas is maintained throughout the additions and for an additional 45 minutes thereafter. Upon addition of the two solutions containing 3, a white precipitate forms. The reaction is allowed to warm to room temperature and to stir for 15 hours. Solvent is removed from the slurry in vacuo. The residue is slurried in water, and the resulting solid is collected by vacuum filtration.

$N^\epsilon$—t—Butoxycarbonyl—lysine—amide, 5.

A solution of the lysine amide 4 (181.48 g, 0.479 mol) in methanol (MeOH, 1000 mL) is added to a catalyst slurry of 5% Pd/C (5 g) in methanol (250 mL) under argon. Hydrogen is bubbled through the reaction mixture (ca. 15 minutes) and the reaction is then stirred under an atmosphere of hydrogen until HPLC analysis indicates that the reaction is complete (36 hours). The hydrogen atmosphere is then displaced with argon. The reaction solution is clarified through a Celite® pad and solvent is removed in vacuo to provide a solid.

$N^\alpha$—Benzyloxycarbonyl—D—phenylalanyl—($N^\epsilon$—t—butoxtcarbonyl) lysine—amide, 8.

$N^\alpha$—Benzyloxycarbonyl—D—phenylalanine (6, 126.39 g, 0.423 mol) is slowly added to a 10° C. solution of CDI (2, 66.03 g, 0.409 mol) in THF (500 mL). Gas evolution is observed during the addition. When gas evolution ceases, the lysine amide 5 (110.75 g, 0.452 mol) is added as a solution in THF (500 mL). After approximately 48 hours the mixture is filtered to remove solids. The filtrate is concentrated in vacuo.

The resulting residue is taken up in ethyl acetate (EtOAc, 500 mL) and is then washed as follows in a separatory funnel:

1. aq HCl (1N, 3×500 mL) pH of wash 1, ca. 8; subsequent wash pH's, 1,
2. water (500 mL),
3. aq Na$_2$CO$_3$(½ saturated, 2×500 mL), is filtered to collect the formed crystalline solids (8),
4. Water (3×500 mL).

The organic layer is dried over MgSO$_4$. After clarification, the solvent is removed in vacuo. The resulting residue can be recrystallized from hot EtOAc to provide a second sample of 8.

D—Phenylalanyl—($N^\epsilon$—t—butoxycarbonyl)lysine—amide, 9.

A methanolic solution (1500 mL) of amide 8 (120.53 g, 0.229 mol) is added to a catalyst slurry of 5% Pd/C (50 g) in MeOH (200 mL). The argon atmosphere is displaced with hydrogen. When HPLC analysis indicates that the reaction is complete (ca. 4 hours), the hydrogen atmosphere is displaced with argon. The reaction solution is then clarified through a Celite® pad and the filtrate is taken to a residue in vacuo. This dipeptide product can be used directly in the preparation of tripeptide 12.

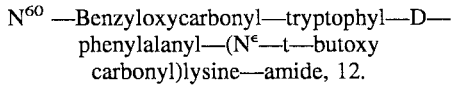

A 10° C. solution of N$^\alpha$—benzyloxycarbonyl-tryptophan (10, 67.60 g, 0.200 mol), THF (500 mL), and CDI (2, 33.05 g, 0.204 mol) is stirred until gas evolution ceases. A solution of 9 (40.8 g, 0.103 mol) in THF (ca. 200 mL) is then added to the reaction mixture. The resulting solution is allowed to react for 15 hours while warming to room temperature. The solid which forms is then collected by vacuum filtration. The filtrate is taken to a residue by concentration in vacuo. The resulting residue and solid are recombined and taken up in EtOAc (4000 mL) with slight warming. Upon cooling the solution to room temperature, a solid forms. The solid is collected by vacuum filtration. This solid is recrystallized from hot MeOH to afford purified tripeptide 12. The EtOAc filtrate (from the first crystallization) is washed as follows in a separatory funnel:

1. aq HCl (1N, 2×500 mL),
2. water (1×500 mL),
3. aq Na$_2$CO$_3$ (½ saturated, 2×500 mL),
4. aq NaCl (1×500 mL).

The organic layer is dried over MgSO$_4$ and then clarified by vacuum filtration. The solvent of the filtrate is removed in vacuo. The resulting residue is again taken up in EtOAc to afford a dry solid. The solid can be subjected to a hot MeOH recrystallization to afford a second crop of 12 as a white solid.

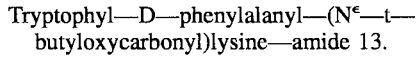

A methanolic solution (1500 mL) of tripeptide 12 (64.59 g, 0.091 mol) is added to a catalyst slurry of 5% Pd/C (5 g) and MeOH (250 mL) under an argon atmosphere. An additional volume of MeOH (2250 mL) is added. The argon atmosphere is displaced with hydrogen and allowed to react (ca. 24 hours). Upon completion of the reaction, the hydrogen atmosphere is displaced with argon. The solution is clarified through a Celite® pad and the filtrate is concentrated in vacuo to provide tripeptide 13 as a white solid.

B. Preparation of Tripeptide
Fragment—K—His—D$^\beta$Nal—Ala—OMe

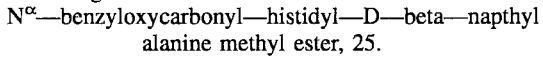

A solution of EtOAc (400 mL) and D—beta—napthylalanine methyl ester hydrochloride (22, 0.62 mol) are washed with saturated sodium carbonate (400 mL) and 0.8N aqueous sodium hydroxide (ca. 500 mL). The resulting aqueous phase is removed (pH 8.5) and the organic phase is sequentially washed with half-saturated aqueous Na$_2$CO$_3$ (150 mL) and then with water (50 mL). The free base form of 22 is isolated upon concentration of the ethyl acetate layer in vacuo.

Dicyclohexylcarbodiimide (DCC, ca. 95 g, 0.46 mol) is added to a −5° C. (ice-ethanol bath) solution of N$^\alpha$—benzyloxycarbonyl—histidine (19, 143.5 g, 0.50 mol), N—hydroxysuccinimide (HONSu, 23, 0.62 mol) and the freshly prepared free base form of 22 (ca. 0.52 mol) in DMF (ca. 3L). The resulting reaction solution is allowed to stir for 24 hours while warming to room temperature. HPLC analysis should be used to see if the reaction is complete. If it is not, the reaction solution is then cooled to ca. −5° C. and an additional portion of dicyclohexylcarbodiimide (ca. 0.17 mol) is added to the reaction. The reaction mixture is then allowed to stir for an additional 24 hours while warming to room temperature. The mixture is then filtered to remove dicyclohexylurea (DCU). Water (1L) is added to the filtrate and the resulting solution is concentrated in vacuo. The resulting residue is taken up in aqueous 1N HCl (ca. 1L until the pH of the aqueous phase reaches a pH of 1). The aqueous phase is then extracted with two portions of ethyl acetate (1L each). The ethyl acetate layers are discarded. The pH of the aqueous phase is then adjusted by addition of cold 2N sodium hydroxide (500 mL) and sodium hydroxide pellets. During this neutralization, the solution is kept cold by addition of cold ethyl acetate (1L). When the pH of the aqueous phase reaches approximately 7, copious precipitation of a white solid or oil usually results. This precipitate is collected by vacuum filtration or decantation and washed sequentially with half saturated sodium carbonate (2×1500 mL), water (6×1500 mL) and ethyl acetate (3×1500 mL). The resulting material is dried under high vacuum to constant weight. This material can be hydrolyzed directly without further purification.

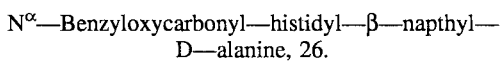

Aqueous sodium hydroxide (192 mL, 0.08 g/mL solution, 0.38 mol) is added to a solution of dipeptide 25 (ca. 0.38 mol), water (360 mL) and MeOH (ca. 6L). The solution is stirred at room temperature until hydrolysis is complete (ca. 24 hours). The disappearance of the starting peptide is established by HPLC analysis. The solution is concentrated in vacuo to a residue which is dissolved in water (ca. 1 L). The aqueous layer (pH ca. 10) is then extracted with EtOAc (2×500 mL) in a separatory funnel. The ethyl acetate layers are discarded. The resulting aqueous phase is adjusted to a pH of approximately 5 with concentrated HCl at which point precipitation of a white solid or oil usually results. The product is collected and is dried in vacuo.

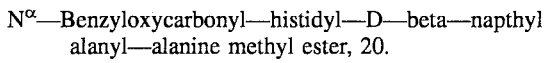

The dipeptide N$^\alpha$—benzyloxycarbonyl—histidyl—D—beta—napthyl alanine (26, 0.253 mol) is added to a solution of the HONSu (23, 0.505 mol) in DMF (800 mL) under an atmosphere of argon. To this solution, a mixture of alanine methyl ester hydrochloride (15, 0.303 mol), N—methylmorpholine (16, 0.303 mol) and DMF (200 mL) is added. The resulting solution is cooled to 10° C., at which time dicyclohexylcarbodiimide (24, 0.265 mol) in methylene chloride (273 mL) is added. The reaction is monitored by HPLC while the reaction temperature is maintained at 10° C. until the reaction is complete. If after several days (ca. 4), the reaction has not progressed to completion, an additional charge of 24 (0.080 mol) is added and the reaction mixture is allowed to stir for an additional day at 10° C. The reaction is again monitored by HPLC analysis until complete (typically ca. 5 days). The solids which form during the reaction are collected by vacuum filtration. The filtrate is then concentrated to a residue in vacuo. The resulting residue is taken up in ethyl acetate and extracted with half-saturated aqueous Na$_2$CO$_3$ (2×500 mL). The ethyl acetate phase is dried over MgSO$_4$. The resulting solution is clarified and is concentrated to a residue in vacuo.

C. Preparation of Tetrapeptide Fragment Ala—His—D$^\beta$Nal—Ala—OH Histidyl—D—beta—Napthyl—Alanyl—Alanine Methyl Ester, 30.

Five percent palladium on carbon (3 g) is carefully added to a solution of N$^\alpha$—benzyloxycarbonyl—histidyl—D—beta—napthyl alanyl—alanine methyl ester20 (71 mmol) in methanol (500 mL) under an argon atmosphere. Argon is bubbled through the reaction mixture for 15 minutes and acetic acid (15 mL, 0.26 mol) is then added. Hydrogen is bubbled (subsurface) through the resulting mixture for 15 minutes and then the reaction is allowed to stir at room temperature under a hydrogen ballast (1 arm). HPLC analysis is then used to monitor how much, if any, starting material remains. If some remains, one carefully bubbles argon through the reaction mixture (subsurface for 30 minutes), and an additional portion of 5% palladium on carbon (2.5 g) is added. Hydrogen is then reintroduced. Argon is again bubbled through the reaction mixture and the resulting solution is clarified by filtration through a pad of diatomaceous earth. The resulting solution is concentrated in vacuo to provide the product. A portion of this product is dissolved or slurried in water (500 mL). Ethyl acetate and saturated aqueous sodium carbonate are added to the resulting material. Isolation of the ethyl acetate layer or the solids which result, provides a material (30) which is free of acetate.

Boc—Alanine N—hydroxysuccinimide ester, 31.

Dicyclohexylcarbodiimide (43 mmol) is added to a room temperature solution of Boc—alanine (43 mmol) and N—hydroxysuccinimide (48 mmol) in methylene chloride (250 mL). The resulting solution is allowed to stir overnight. The reaction mixture is then filtered to remove dicyclohexylurea and the clarified filtrate is concentrated in vacuo to provide the product, which is stored at −20° C. under an argon atmosphere prior to use.

Boc—Ala—His—D—B$^\beta$Nal—Ala—OMe, 32.

The above alanine ester (23.9 mmol) is added to a solution of His—D—$^\beta$Nal—Ala—OMe (30) (20.1 mmol) in anhydrous dimethylformamide (DMF, 200 mL). The resulting homogeneous solution is allowed to stir over the weekend at room temperature and monitored. When HPLC analysis indicates that virtually no tripeptide remains in the reaction mixture (e.g., about 3 days), water (50 mL) is added to the reaction and the resulting mixture is allowed to stir for an additional day. This solution is then concentrated in vacuo. The resulting residue is dissolved in ethyl acetate and is then extracted with half-saturated aqueous sodium carbonate (2×300 mL). The organic phase is dried with MgSO$_4$ and Na$_2$SO$_4$ and is concentrated in vacuo to provide the tetrapeptide. This material is used without further purification in the preparation of Boc—Ala—His—D—$^\beta$Nal—Ala—OH.

Boc—Ala—His—D—$^\beta$Nal—Ala—OH, 33.

A 2N aqueous sodium hydroxide solution (7.5 mL, 15 mmol) is added to a methanol (500 mL) and water solution (200 mL) containing Boc—Ala—His—D—$^\beta$Nal—Ala—OMe (13.7 mmol). After the reaction is allowed to stir overnight at room temperature, HPLC analysis indicates the amount of the starting material remaining. When it is essentially complete (ca. overnight), the resulting solution is concentrated in vacuo to a volume of approximately 200 mL. Water (100 mL) is added and the pH is adjusted to approximately 12 by addition of 2N sodium hydroxide (1 mL). The resulting solution is extracted with ethyl acetate (2×500 mL). The ethyl acetate layers are discarded. The pH of the aqueous phase is then adjusted to approximately 5 by addition of aqueous HCl which usually results in the precipitation of the product. It is important to minimize the volume of the aqueous phase to promote this precipitation. The aqueous phase is decanted away from the product and the product is then rinsed with water (2×50 mL). The isolated product is dried to constant weight in vacuo.

D. Condensation Reaction of Peptide Fragments to Produce Heptapeptide
Boc—Ala—His—D$^\beta$Nal—Ala—Trp—D—Phe—Lys(Boc)—NH$_2$, 34.

The two peptides Boc—Ala—His—D—$\beta$Nal—Ala—OH (33, 2.6 mmol) and Trp—D—Phe—Lys(Boc)—NH$_2$ (13, 2.8 mmol) are dissolved in anhydrous DMF and the resulting solution is concentrated in vacuo. This preliminary concentration is carried out in an attempt to remove any traces of methanol which might be present. The resultant peptide mixture is redissolved in DMF and N—hydroxysuccinimide (5.1 mmol) is then added. The resulting solution is then cooled to a solution temperature of −2° C. and dicyclohexylcarbodiimide (3.4 mmol) is then added as a solution in methylene chloride (3.5 mL). The resulting reaction mixture is allowed to stir at −2° C. solution temperature for a period of three days. HPLC analysis is used to determine if the reaction is essentially completed. After this period of time, if it is not, additional dicyclohexylcarbodiimide can then be added and the resultant reaction mixture allowed to stir for an additional day at −2° C. If, on the following day (for a total of four days) HPLC analysis again indicates incomplete reaction, cooling of the reaction mixture should be terminated. The solution temperature of the reaction can be allowed to slowly rise to room temperature (25° C.) over a period of hours (ca. 8). The resultant reaction mixture is allowed to stir overnight at room temperature. The procedure is repeated until the reaction is complete. Then, water (50 mL) is added and the resulting mixture is allowed to stir for an additional day. The reaction solution is then filtered to remove dicyclohexylurea and the resulting filtrate is concentrated in vacuo to a viscous oil. Ethyl acetate and half-saturated aqueous sodium carbonate (200 mL) are added to the resulting residue. The two-phase mixture is vigorously swirled on a rotary evaporator for approximately one hour. Any solids formed are collected to provide the product by filtration on a scintered glass funnel. The organic phase is washed with water and then dried to constant weight in vacuo to provide the product.

Ala—His—D—$^\beta$Nal—Ala—Trp—D—Phe—Lys—NH$_2$, 35.

The heptapeptide Boc—Ala—His—D—$^\beta$Nal—Ala—Trp—D—Phe—Lys —(Boc)—NH$_2$ (34, 1.02 mmol) is added to a room temperature solution of trifluoroacetic acid (30 mL), dimethylsulfide (14 mL), 1,2 ethanedithiol (7 mL) and anisole (2.2 mL) in methylene chloride (15 mL). The homogeneous reaction mixture is allowed to stir for 15 minutes. After this period of time, anhydrous ether (450 mL) is added to cause precipitation of the crude biologically active peptide product 35. This product is isolated by filtration on a scintered glass funnel or by decantation. The resultant product is dissolved in water and lyophilized. The lyophilized product can be further purified by medium pressure chromatography on a 26×460 mm glass column containing Lichroprep™ RP—18 column packing material (C-18, 25–40 nm, irregular mesh). After injection of the peptide as a solution in water, the column is eluted at a flow rate of 9 mL per minute with a shallow gradient of 0 to 25% methanol for 5–20 hours, and then by a gradient of 25 to 55% methanol over ca. 48 hours. The methanol concentration of the gradient is then increased at a rate of 2% per hour. During the elution, the remainder of the solvent composition is made up of water containing 0.2% trifluoroacetic acid. The product (35) is identified by HPLC and is isolated by concentration of the appropriate elution volumes.

The invention has been described in detail with particular reference to preferred embodiments thereof. However, it will be appreciated that those skilled in the art, upon consideration of this disclosure may make variations and modifications within the spirit and scope of the invention.

We claim:

1. A peptide having the formula

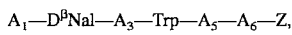

$A_1 - D^\beta Nal - A_3 - Trp - A_5 - A_6 - Z$, wherein $A_1$ is His, 3(NMe)His, His—Ala, Ala, Tyr, $A_0$—His or $A_0$—3(NMe)His, where $A_0$ is Ala, Lys, or Glu Met(O), DOPA, Abu or peptides of the formula L—$A_0$, wherein L is H, DOPA, Lys, Phe, Tyr, Cys, Tyr—DAla—Phe—Gly, Tyr—DAla—Gly—Phe, Tyr—Ala—Gly—Thr or Tyr—DAla—Phe—Sar;

$A_3$ is Ala, Gly or Ser;

$A_5$ is DPhe, D/L$^\beta$(Me)Phe or (NMe)DPhe;

$A_6$ is Arg, iLys, Lys or Orn;

Z is $NH_2$;

and organic or inorganic pharmaceutically acceptable salts thereof.

2. The peptide according to claim 1, wherein $A_1$ is His, Ala, His—Ala or $A_0$—His.

3. The peptide according to claim 1, wherein $A_0$ is Ala, Lys, or Glu; $A_3$ is Ala; $A_6$ is Lys, or iLys.

4. The peptide according to claim 1, wherein $A_3$ is Ala.

5. The peptide according to claim 1 having the formula His—D$^\beta$Nal—Ala—Trp—DPhe—$A_6$—Z.

6. The peptide according to claim 1 having the formula $A_0$—His—D$^\beta$Nal—Ala—Trp—DPhe—$A_6$—Z.

7. The peptide according to claim 1 having the formula Lys—His—D$^\beta$Nal—Ala—Trp—DPhe—$A_6$—$NH_2$.

8. The peptide according to claim 1 having the formula Glu—His—D$^\beta$Nal—Ala—Trp—DPhe—$A_6$—$NH_2$.

9. The peptide according to claim 1 having the formula His—Ala—D$^\beta$Nal—Ala—Trp—DPhe—$A_6$—Z.

10. The peptide according to claim 1 having the formula His—Ala—D$^\beta$Nal—Ala—Trp—DPhe—Lys—$NH_2$.

11. The peptide according to claim 1 having the formula Ala—D$^\beta$Nal—Ala—Trp—DPhe—$A_6$—Z.

12. The peptide according to claim 1 having the formula Ala—D$^\beta$Nal—Ala—Trp—DPhe—Lys—$NH_2$.

13. The peptide having the formula His—D$^\beta$Nal—Ala—Trp—DPhe—Lys—$NH_2$.

14. The peptide having the formula Ala—His—D$^\beta$Nal—Ala—Trp—DPhe—Lys—$NH_2$.

15. A peptide having the formula Ala—His—D$^\beta$Nal—Ala—Trp—DPhe—Ala—Lys—$NH_2$.

16. A peptide having the formula Ala—His—D$^\beta$Nal—Ala—Trp—DPhe—Ala—Ala—Lys—$NH_2$.

17. A method of promoting the release of growth hormone levels in an animal comprising administering to the animal an effective amount of at least one of the peptides of claims 1, 4, 5, 6, 9, 11, 13, 14 or 15.

18. The method of claim 17, wherein the animal is a mammal.

19. The method of claim 17, wherein the animal is a human.

20. A pharmaceutical composition for promoting the release of growth hormone levels in animals comprising at least one of the peptides of claim 1, 3, 5, 6, 9, 11, 13, 14 or 15 and a pharmaceutically acceptable carrier or diluent.

21. The pharmaceutical compositions of claim 20, which further comprises a second compound, wherein said second compound is a Group 1 or Group 3 compound.

22. The pharmaceutical composition of claim 21, wherein the second compound is Tyr—Ala—Asp—Ala—Ile—Phe—Thr—Asn—Ser—Tyr—Arg —Lys—Val—Leu—Gly—Gln—Leu—Ser—Ala—Arg—Lys—Leu—Leu—Gln—Asp—Ile—Nle —Ser—Arg—$NH_2$, or Tyr—DArg—Phe—Gly—$NH_2$.

23. A method of promoting the release and elevation of blood growth hormone levels by administering the peptide of claim 1 in an effective amount with a second compound, wherein said second compound is a Group 1 or Group 3 compound.

24. The method of claim 23, wherein the second compound is Tyr—Ala—Asp—Ala—Ile—Phe—Thr—Asn—Ser—Tyr—Arg—Lys—Val—Leu—Gly—Gln —Leu—Ser—Ala—Arg—Lys—Leu—Leu—Gln—Asp—Ile—Nle—Ser—Arg—$NH_2$, or Tyr —DArg—Phe—Gly—$NH_2$.

* * * * *